(12) United States Patent
Werzer et al.

(10) Patent No.: US 9,330,408 B2
(45) Date of Patent: May 3, 2016

(54) SYSTEM, ASSEMBLY, AND METHOD FOR PROVIDING CORRECTIVE EYEWEAR

(71) Applicant: EYEMPOWER, LLC, Fort Lauderdale, FL (US)

(72) Inventors: Michael Stewart Werzer, Fort Lauderdale, FL (US); Howard Lesser, Plantation, FL (US); Scott Fred Levine, Fort Lauderdale, FL (US); Kevin Lesser, Plantation, FL (US); Brett Rose, Fort Lauderdale, FL (US); Jeremiah Gutierrez, Fort Lauderdale, FL (US)

(73) Assignee: EYEMPOWER, LLC, Fort Lauderdale, FL (US)

( * ) Notice: Subject to any disclaimer, the term of this patent is extended or adjusted under 35 U.S.C. 154(b) by 0 days.

(21) Appl. No.: 14/302,719

(22) Filed: Jun. 12, 2014

(65) Prior Publication Data

US 2015/0363853 A1    Dec. 17, 2015

(51) Int. Cl.
G06Q 30/06    (2012.01)
A61B 3/11    (2006.01)
G02C 13/00    (2006.01)
A61B 3/14    (2006.01)

(52) U.S. Cl.
CPC ............ *G06Q 30/0621* (2013.01); *A61B 3/111* (2013.01); *G02C 13/005* (2013.01); *G06Q 30/0635* (2013.01); *A61B 3/14* (2013.01); *G02C 13/003* (2013.01); *G06Q 30/0601* (2013.01); *G06Q 30/0603* (2013.01)

(58) Field of Classification Search
CPC .......... G06Q 30/0621; G06Q 30/0601; G06Q 30/0603; G06Q 30/0643; A61B 3/111; A61B 3/14; G02C 13/005; G02C 13/003

USPC ............................................. 705/26.5; 351/25
See application file for complete search history.

(56) References Cited

U.S. PATENT DOCUMENTS

| 5,983,201 | A | 11/1999 | Fay |
| 6,095,650 | A * | 8/2000 | Gao ..................... G02C 13/005 351/227 |
| 6,508,553 | B2 | 1/2003 | Gao et al. |
| 6,535,223 | B1 * | 3/2003 | Foley ..................... A61B 3/111 345/629 |

(Continued)

FOREIGN PATENT DOCUMENTS

DE    19752729    6/1999

OTHER PUBLICATIONS

GLASSES2YOU, How to shop online for Prescription Glasses—Pupillary Distance, Sep. 20, 2013, United Kingdom.

(Continued)

*Primary Examiner* — Yogesh C Garg
(74) *Attorney, Agent, or Firm* — The Concept Law Group, P.A.; Scott D. Smiley; Yongae Jun

(57) ABSTRACT

A method of providing corrective eyewear is disclosed, the method including providing a kiosk having a plurality of eyeglass frame. The plurality of eyeglass frames vary in at least one of a dimension and a size from one another and each of the plurality of eyeglass frames has at least one reference dimension on a body of the eyeglass frame. The method further includes receiving a digital image of the consumer wearing a selected eyeglass frame and determining a pupillary distance of the consumer based on the digital image and the at least one reference dimension of the consumer-selected eyeglass frame.

5 Claims, 9 Drawing Sheets

(56) References Cited

U.S. PATENT DOCUMENTS

| | | |
|---|---|---|
| 6,791,584 B1 | 9/2004 | Xie |
| 6,792,401 B1 * | 9/2004 | Nigro .................. G02C 13/003 703/6 |
| 7,322,697 B2 | 1/2008 | Jojiki |
| 7,982,750 B2 | 7/2011 | Xie |
| 8,459,792 B2 | 6/2013 | Wilson et al. |
| 2003/0081173 A1 * | 5/2003 | Dreher ........................ 351/204 |
| 2004/0004633 A1 * | 1/2004 | Perry ................. G06Q 30/0603 715/728 |
| 2006/0290885 A1 * | 12/2006 | Covannon et al. ............ 351/212 |
| 2008/0012936 A1 * | 1/2008 | White ....................... 348/14.16 |
| 2011/0288938 A1 * | 11/2011 | Cook et al. ................. 705/14.66 |
| 2012/0016763 A1 * | 1/2012 | Kirschner .................... 705/26.5 |
| 2012/0307196 A1 * | 12/2012 | Lin ......................... G02C 1/06 351/83 |
| 2013/0262259 A1 * | 10/2013 | Xie ....................... G02C 7/086 705/26.5 |
| 2015/0088307 A1 * | 3/2015 | Ackerman ........... G06Q 10/087 700/241 |

OTHER PUBLICATIONS

PDCAPTURE, How to Measure Pupillary Distance, Sep. 20, 2013, United States.

\* cited by examiner

SYSTEM, ASSEMBLY, AND METHOD FOR PROVIDING CORRECTIVE EYEWEAR

FIELD OF THE INVENTION

The present invention relates generally to corrective eyewear and, more particularly, relates to an automated provider system that provides custom fit corrective eyewear to purchasers.

BACKGROUND OF THE INVENTION

As is known in the art, when ordering prescription glasses, the user's pupillary distance, i.e., the distance between the user's pupils, must be known in order to properly construct the glasses. There is a variance of this distance from person to person and proper sight correction can only be achieved if this distance is taken into account.

Additionally, there is a growing popularity among consumers to purchase corrective eyewear through venues other than a physical retail location employing an eye care professional, such as an optician. For example, corrective eyewear is currently sold over the Internet. However, there is a problem with Internet ordering in that consumers are not able to physically try on the eyeglass frames before purchase. Many consumers find it difficult to make a confident decision on a frame style without physically trying on the eyeglass frame and seeing how it looks on their face.

Another difficulty with ordering corrective eyewear over the Internet is measuring a pupillary distance of the consumer. The pupillary distance is the measurement of the distance from one pupil to the other pupil. The measurement is preferably taken from a location within one pupil to the same location within the other pupil. For example, the measurement should be taken from an edge of one pupil to a corresponding edge of the other pupil; or from a center of one pupil to the center of the other pupil. The pupillary distance is required for preparation of the eyeglass lenses. The pupillary distance measurement allows the lens preparer to align the center of focus on a corrective lens with the center of the consumer's pupils. Prior-art methods of measuring the pupillary distance of the consumer include: Contacting an optician, an optometrist, or other eye care professional to measure the pupillary distance at an optician's physical location; the consumer measuring the pupillary distance with a ruler; or capturing an image of a reference object, e.g., compact disc, held proximate to the consumer's face for measuring the pupillary distance relative to the reference object. However, consumers find it inconvenient and costly to visit an eye care professional. At the same time, many consumers find it difficult and cumbersome to measure their own pupillary distance. There is also a risk that the measurement will be inaccurate. This can result in the consumer receiving corrective eyewear that is inaccurately prepared and, therefore, does not correct the consumer's vision.

Capturing an image of the consumer's face proximate a reference object is also inconvenient because the consumer may not have the particular reference object on hand and, again, the consumer may position the reference object incorrectly. Typically, in order to accurately measure pupillary distance the reference object is placed on the same plane as the consumer's face so that the distance between the reference object and the camera lens is the same as the distance between the consumer's face and the camera lens. Inaccurately placing the reference object, respective to the consumer's face, can also result in an inaccurate measurement of the pupillary distance.

Therefore, a need exists to overcome the problems with the prior art as discussed above.

SUMMARY OF THE INVENTION

The invention provides an apparatus and method for providing corrective eyewear that overcomes the hereinafore-mentioned disadvantages of the heretofore-known devices and methods of this general type.

With the foregoing and other objects in view, there is provided, in accordance with the invention, a method of ordering corrective eyewear is disclosed. The method includes receiving, at an electronic kiosk, a digital image of a consumer wearing a consumer-selected eyeglass frame, the digital image including at least one reference dimension of the consumer-selected eyeglass frame and a pair of pupils of the consumer. The electronic kiosk contains a plurality of eyeglass frames varying in at least one of a dimension and a size from one another. The electronic kiosk determines a pupillary distance of the consumer based on a predetermined value of the reference dimension of the consumer-selected eyeglass frame, the predetermine value stored in a database communicatively coupled to the electronic kiosk. The electronic kiosk communicates an identifier associated with the consumer-selected eyeglass frame and the determined pupillary distance of the consumer to a computer for ordering a corrective eyeglass frame and lens assembly corresponding to the consumer-selected eyeglass frame and the determined pupillary distance of the consumer.

In accordance with an embodiment of the present invention, the reference dimension can be a length of a front frame; a length of a single lens frame; a height of a lens frame; and/or a bridge length.

In accordance with another feature, the reference dimension includes at least two reference dimensions.

In accordance with another feature, an embodiment of the present invention includes obtaining a prescription information input by the consumer via a user input interface included in the electronic kiosk.

In accordance with a further feature of the present invention, an embodiment includes identifying the consumer-selected eyeglass frame using the digital image.

In accordance with a further feature of the present invention, an embodiment includes identifying the consumer-selected eyeglass frame by receiving an identification code input by the consumer via a user input interface included in the electronic kiosk.

In accordance with another feature, an embodiment of the present invention also includes providing the electronic kiosk at a retail location that does not employ an eye care professional associated with the electronic kiosk.

In accordance with another feature, the electronic kiosk includes an image capturing device behind a two-way mirror.

In accordance with yet another feature, the electronic kiosk is a self-contained unit substantially enclosed by a housing.

In accordance with another feature, an embodiment of the present invention includes requiring the consumer to provide at least one of a payment input and an identification input prior to the electronic kiosk releasing the consumer-selected one of the plurality of eyeglass frames from the housing.

In accordance with yet another feature, the kiosk includes a viewing panel, at least one image capturing unit, a transaction control unit, and a financial transaction unit.

In accordance with the present invention, an electronic kiosk assembly for ordering corrective eyewear is disclosed. The electronic kiosk assembly includes an eyeglass frame support for supporting a plurality of eyeglass frames, the plurality of eyeglass frames varying in a dimension and a size from one another and each of the plurality of eyeglass frames having at least one reference dimension on a body of the eyeglass frame. The electronic kiosk assembly further includes a computer readable medium, having an executable instruction set configured to perform steps of receiving, at the electronic kiosk assembly, a digital image of a consumer wearing a consumer-selected eyeglass frame, the digital image including the at least one reference dimension of the consumer-selected eyeglass frame and a pair of pupils of the consumer. The executable instruction set is further configured to perform the step of determining a pupillary distance of the consumer based on a predetermined value of the reference dimension of the consumer-selected eyeglass frame, the predetermine value stored in a database communicatively coupled to the electronic kiosk assembly. The executable instruction set is further configured to perform the step of communicating an identifier associated with the consumer-selected eyeglass frame and the determined pupillary distance of the consumer to a computer for ordering a corrective eyeglass frame and lens assembly corresponding to the consumer-selected eyeglass frame and the determined pupillary distance of the consumer.

In accordance with another feature, the computer readable medium further includes an executable instruction set configured to perform a step of requiring the consumer to provide a payment input and/or an identification input prior to the electronic kiosk releasing the consumer-selected eyeglass frame from the housing.

In accordance with yet another feature, the electronic kiosk assembly further includes a viewing panel, an image capturing unit, a transaction control unit, and a financial transaction unit.

In accordance with a further feature of the present invention, a method of ordering corrective eyewear for a consumer is disclosed. The method includes selecting one of a plurality of eyeglass frames provided at an electronic kiosk, the plurality of eyeglass frames varying in a dimension and/or a size from one another and each of the plurality of eyeglass frames having at least one reference dimension on a body of the eyeglass frame. A predetermined value of each of the reference dimensions is stored at a database communicatively coupled to the electronic kiosk and the predetermined value is associated with a corresponding eyeglass frame. The method further includes placing the selected eyeglass frame on a consumer's face; while wearing the selected eyeglass frame, capturing a digital image of the consumer's face with a camera located at the electronic kiosk; and ordering a corrective eyewear assembly at the electronic kiosk, the corrective eyewear assembly including the selected eyeglass frame and a lens operably configured according to a pupillary distance determined from the predetermined value of the reference dimension of the selected eyeglass frame.

In accordance with another feature, an embodiment of the present invention includes inputting a prescription information input via a user input interface included in the electronic kiosk.

In accordance with yet another feature, an embodiment of the present invention includes inputting an identification code associated with the selected eyeglass frame via a user input interface included in the electronic kiosk.

In accordance with a further feature, an embodiment of the present invention includes traveling to the electronic kiosk at a retail location that does not employ an eye care professional associated with the electronic kiosk.

In accordance with another embodiment of the present invention, there is provided a method of determining pupillary distance. The method includes receiving a digital image of a consumer wearing a consumer-selected one of a plurality of eyeglass frames, the digital image including at least one reference dimension of the consumer-selected eyeglass frame and a pair of pupils of the consumer. An identifier associated with the consumer-selected eyeglass frame is communicated to a computer communicatively coupled to a database. The database stores at least one predetermined value of at least one reference dimension of each of the plurality of eyeglass frames, the plurality of eyeglass frames varying in a dimension and a size from one another. A predetermined value of the reference dimension of the consumer-selected eyeglass frame is received from the database. A pupillary distance of the consumer is determined based on the predetermined value of the reference dimension of the consumer-selected eyeglass frame.

Although the invention is illustrated and described herein as embodied in an assembly and method for providing corrective eyewear, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. The terms "program," "software application," and the like as used herein, are defined as a sequence of instructions designed for execution on a computer system. A "program," "computer program," or "software application" may include a subroutine, a function, a procedure, an object method, an object implementation, an executable instruction set, an executable application, an applet, a servlet, a source code, an object code, a shared library/dynamic load library and/or other sequence of instructions designed for execution on a computer system. The term "kiosk," as used herein, indicates any small structure or small housing intended for display in a public area for retailing a good and/or a service.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
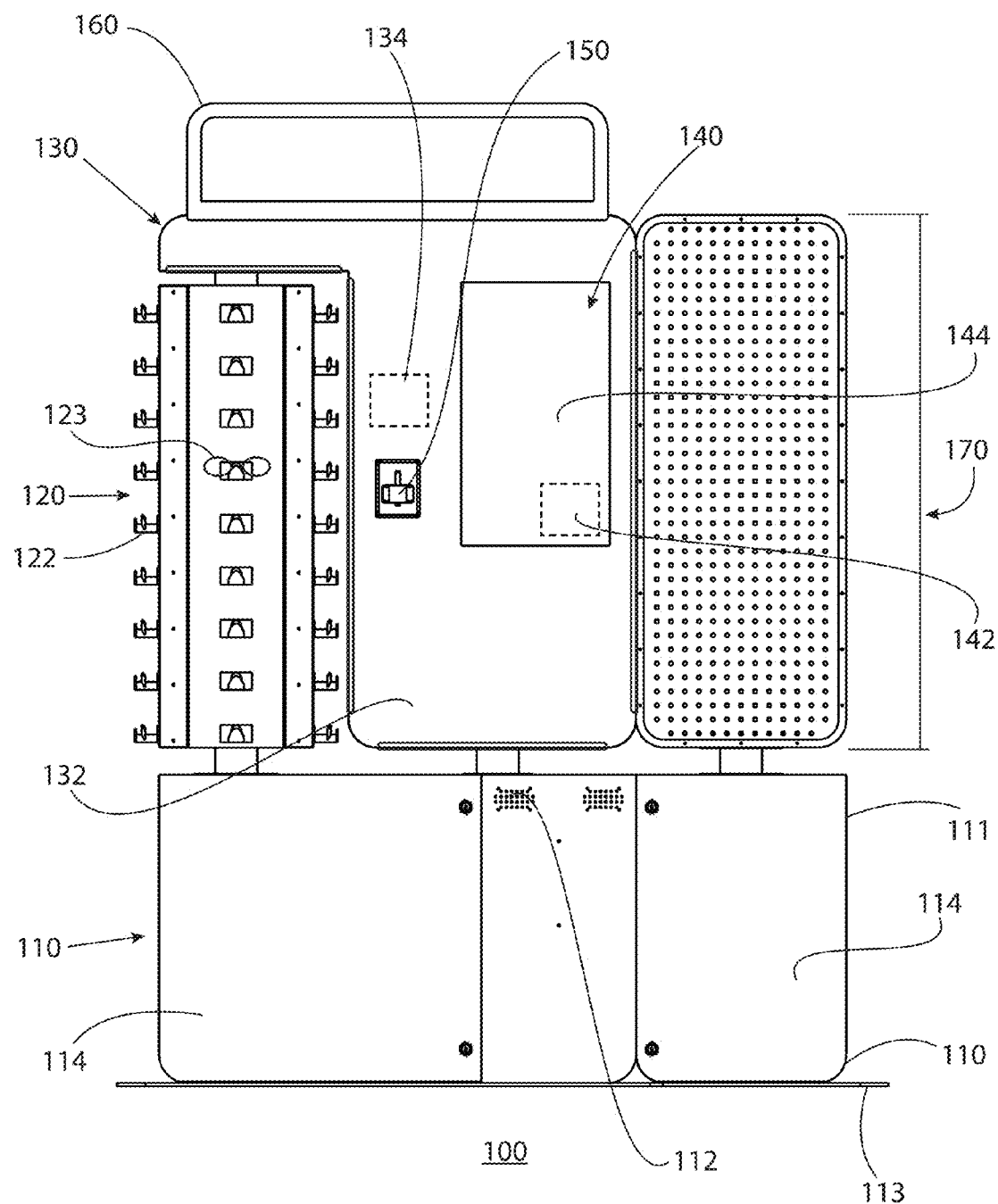
FIG. 1 is a front elevation view of a corrective eyewear kiosk in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient system, assembly, and method of providing corrective eyewear conveniently to a user. Embodiments of the invention provide a kiosk for ordering corrective eyewear including a framework for supporting a plurality of eyeglass frames varying in dimension and size; a camera for capturing an image of a consumer wearing a selected eyeglass frame; and an instruction set stored in memory, the instruction set being executable by a processor to calculate the pupillary distance of the consumer using the captured image and a known reference dimension of the selected eyeglass frame. In addition, embodiments of the invention provide a system and method of storing a known reference dimension of each of the plurality of eyeglass frames in a database.

Referring now to FIG. 1, one embodiment of the present invention is shown in a front elevation view. FIG. 1 shows several advantageous features of the present invention, but, as will be described below, the invention can be provided in several shapes, sizes, combinations of features and components, and varying numbers and functions of the components. The first example of a corrective eyewear electronic kiosk 100, as shown in FIG. 1, includes a kiosk base 110, an eyeglass frame support 120, a kiosk ordering station 130, a signage device 160, and a product display board 170.

Figure 2:
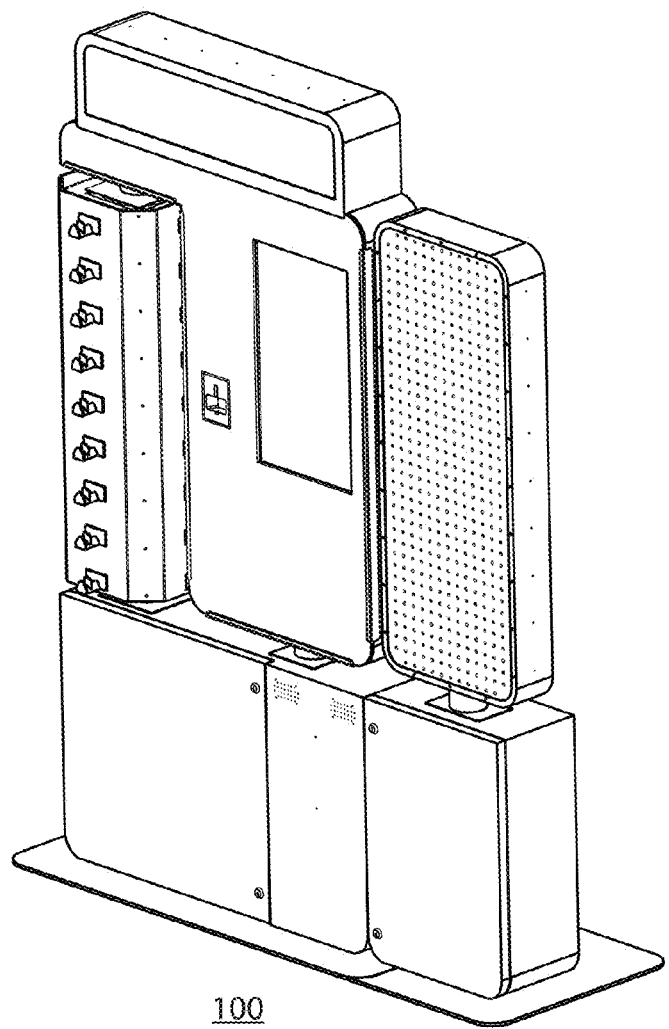
FIG. 2 is a perspective view of the corrective eyewear kiosk of FIG. 1 in accordance with the present invention.
Figure 3:
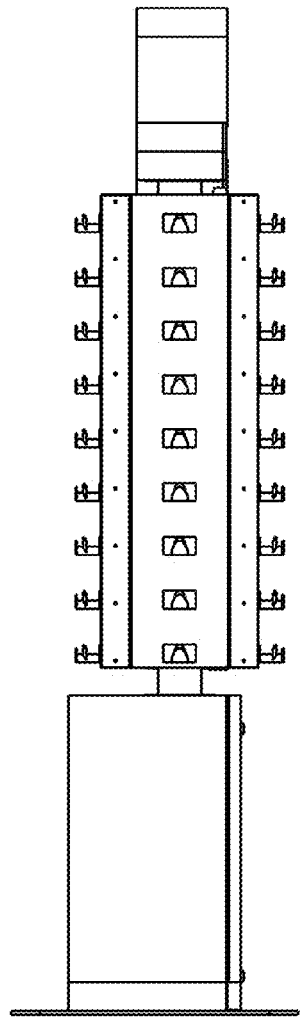
FIG. 3 is a side elevation view of the corrective eyewear kiosk of FIG. 1 in accordance with the present invention.

Referring generally to FIGS. 1-3, the kiosk base 110 includes a housing 111 and a ground-engaging panel 113. The housing 111 may include a pair of speakers 112 and a pair of storage compartments 114 for storing items, such as additional eyeglass frames.

The eyeglass frame support 120 includes a plurality of support members 122, each of the plurality of support members 122 are operably configured to support an eyeglass frame 123. The plurality of support members 122 can be arranged in adjacent vertical rows on the walls of the eyeglass frame support 120. The eyeglass frame support 120 is preferably rotatable about a central axis for allowing a consumer convenient access to each side of the support structure 120. The eyeglass frame support 120 can be provided in the form of a rack, shelf, rotatable carousel, and the like.

The kiosk ordering station 130 is centrally disposed between the eyeglass frame support 120 and the product display board 170. The kiosk ordering station 130 is operably configured to allow the consumer to capture of an image of a selected eyeglass frame 123, initiate an order for a corrective eyewear assembly, and/or provide payment. The kiosk ordering station 130 includes a viewing panel 132, an image capturing unit 134, a transaction control unit 140, and a financial transaction unit 150. The viewing panel 132 provides a surface on which the consumer may view an image of himself wearing the selected eyeglass frame 123 in order to decide if the selected frame 123 is aesthetically pleasing to the consumer. In the exemplary embodiment, the viewing panel 132 is provided on a front surface of the ordering station 130 and is formed of a reflective surface, such as a glass mirror. In another embodiment, the viewing panel 132 may be formed as a display of a computer, such as a computer tablet with a camera having video capability. The camera can capture video of the consumer at the ordering station 130 via a lens facing toward the consumer and the display can present the captured video in real-time to the consumer via the display.

The image capturing unit 134 is in the form of a camera configured to capture a digital image of the consumer wearing the selected eyeglass frame 123. In the exemplary embodiment, the viewing panel 132 is formed as a two-way mirror. The two-way mirror includes a reflective surface and an opposing transparent surface. The image capturing unit 134 is positioned behind the two-way mirror, on the side of the transparent surface. Accordingly, a lens on the image capturing unit 134 can capture a still image of the consumer standing in front of the reflective surface of the two-way mirror, while at the same time, permitting the consumer to view himself wearing the eyeglass frame 123 via the reflective surface of the mirror, without requiring a resource-heavy video feed, as in other embodiments. In an alternative embodiment, the corrective eyewear electronic kiosk 100 can include two or more cameras.

The transaction control unit 140 can operate as a control panel provided on a front surface of the ordering station 130. The transaction control unit 140 can be a computer that allows for the input of customer information and control commands via a processor 142. In the exemplary embodiment, the transaction control unit 140 is formed as a computing device including the processor 142 and a display 144. The processor 142 can be a central processing unit (CPU), microcontroller, or microprocessor, including a "general purpose" microprocessor or a special purpose microprocessor. The processor 142 executes code stored in memory in order to carry out operation of the transaction control unit 140. The processor 142 may provide the processing capability to execute an operating system, run various applications, and provide processing for one or more of the techniques described herein.

The display 144 displays information to the consumer such as menus, icons, or the like, prompting the consumer to capture an image; view the image captured; input prescription information; initiate an order of corrective eyewear; provide payment information; input consumer identification information, such as name and address; or the like. In some embodiments, instructions provided to the consumer may be provided as audible signals via the speakers 112. The display 144 may be any type of suitable display, such as a liquid-crystal display (LCD), a plasma display, a light-emitting diode (LED) display, or the like. The display 144 can be operably configured as a user input interface, such as a touchscreen.

The user input interface facilitates interaction between the consumer and the kiosk ordering station 130 by allowing the consumer to enter input through keys or buttons provided on the touchscreen. In other embodiments, there can be provided other types of user input interfaces, such as, for example, a keyboard, a keypad, a mouse, or the like. The user input interface may include alphanumeric keys for allowing entry of alphanumeric information (e.g. telephone numbers, contact information, text, etc.). The user input interface may include special function keys (e.g. a camera shutter button, volume control buttons, back buttons, home button, etc.), navigation and select keys, a pointing device, and the like.

The transaction control unit 140 can include a network interface feature, such as a Wi-Fi card that facilitates connection to the Internet, or another network interface card that facilitates a connection to another network, such as a local area network (LAN) or another wide area network (WAN). The transaction control unit 140 can further include memory, such as, for example, one or more buffers, registers, random access memory (RAM), and non-volatile memory, such as a hard disk drive, Flash Memory, or the like, to store information, data, and/or software instructions.

The financial transaction unit 150 receives payment information from the consumer. In the exemplary embodiment, the financial transaction unit 150 is formed as an electronic payment reader, such as a credit card or debit card reader. The electronic payment reader allows the consumer to provide payment information for ordering corrective eyewear at the corrective eyewear electronic kiosk 100 by swiping his credit card through the reader. In another embodiment, there may be provided a slot or other opening at the electronic kiosk 100 that allows consumers to feed paper money or coins into the electronic kiosk 100 to provide payment.

The signage device 160 can be provided in an upper section of the corrective eyewear electronic kiosk 100 for maximum visibility to a multitude of potential customers. The signage device 160 can display, for example, the name of the business entity providing the electronic kiosk 100, a trademark associated with the electronic kiosk 100, information about current sales or specials, or the like.

The product display board 170 is in the form of a back-lit pinboard. The product display board 170 provides an alternative support structure for displaying eyeglass frames 123. The back-lighting feature provides an attractive feature for drawing the attention of potential customers to the corrective eyewear electronic kiosk 100.

Figure 4:
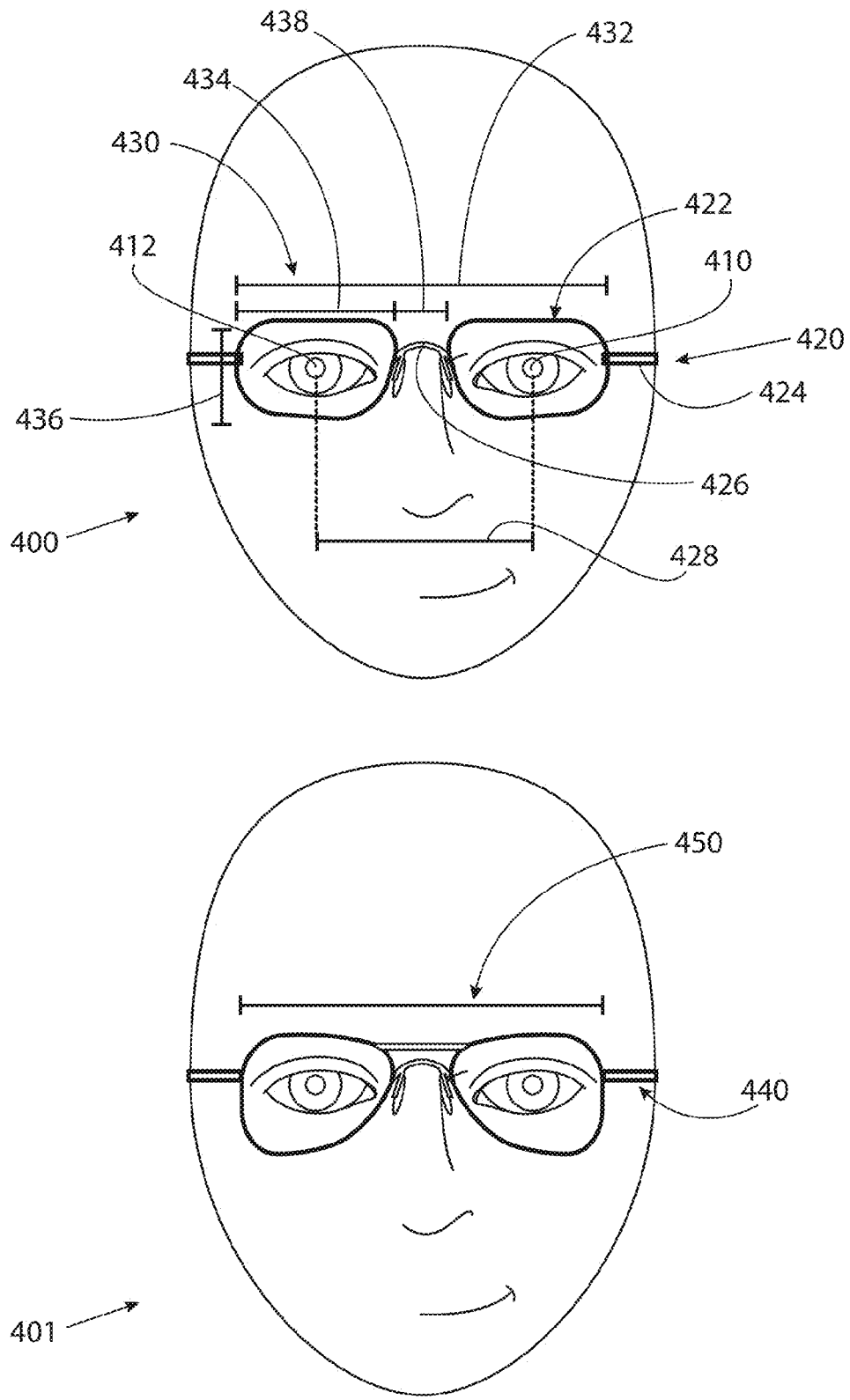
FIG. 4 is a schematic diagram of an image of a consumer wearing an eyeglass frame and illustrating reference dimensions and a pupillary distance in accordance with the present invention.

Referring now primarily to FIG. 4, a schematic diagram of an image of a consumer 400 wearing a first selected eyeglass frame 420 in accordance with the present invention is presented. The eyeglass frame 420 body includes a pair of lens frames 422, a pair of side arms 424 extending therefrom, and a bridge 426 extending between each lens frame 422. The image captured from the image capturing unit 134 includes the consumer's face 400, showing the consumer's pupils 410, 412 and the eyeglass frame 420. The eyeglass frame 420 includes one or more reference dimension(s) 430 that can be used to mathematically calculate the distance between the customer's pupils 410, 412, i.e. the pupillary distance 428. The reference dimension(s) 430 can include a length of the front frame 432, the front frame 432 including the lengths of each lens frame plus the length of the bridge; a length of one lens frame 434; a height of one lens frame 436; and/or a bridge length 438. Other reference dimensions 430 of the eyeglass frame 420 can be used, as well. A predetermined value representing each of the reference dimensions 430 is stored in a database communicatively coupled to the corrective eyewear electronic kiosk 100, such as a non-volatile memory device included in the corrective eyewear electronic kiosk 100, and/or another database that is remotely located but that is communicatively coupled to the electronic kiosk 100 by, for example, a wireless network. The processing unit 142 can calculate the pupillary distance 428 using the captured digital image and at least one predetermined value of at least one reference dimension 430 associated with the eyeglass frame 420 worn by the consumer 400 in the digital image. In an alternative embodiment, this calculation can be performed by a remotely located processing unit.

A second consumer 401 can decide to order a second eyeglass frame 440 having a dimension and a size different from the dimension and size of the first eyeglass frame 420 selected by the first consumer 400. Accordingly, the predetermined value(s) stored in the database representing the reference dimension(s) 450 of the second eyeglass frame 440 are different from the predetermined value(s) associated with the first eyeglass frame 420. Advantageously, providing predetermined reference dimensions 430 associated with each eyeglass frame 420 at the electronic kiosk 100 permits calculation of the pupillary distances of consumers selecting different style eyeglass frames, without the need for a separate object, such as a compact disc, to be captured in the image, as in some prior art methods.

Figure 5:
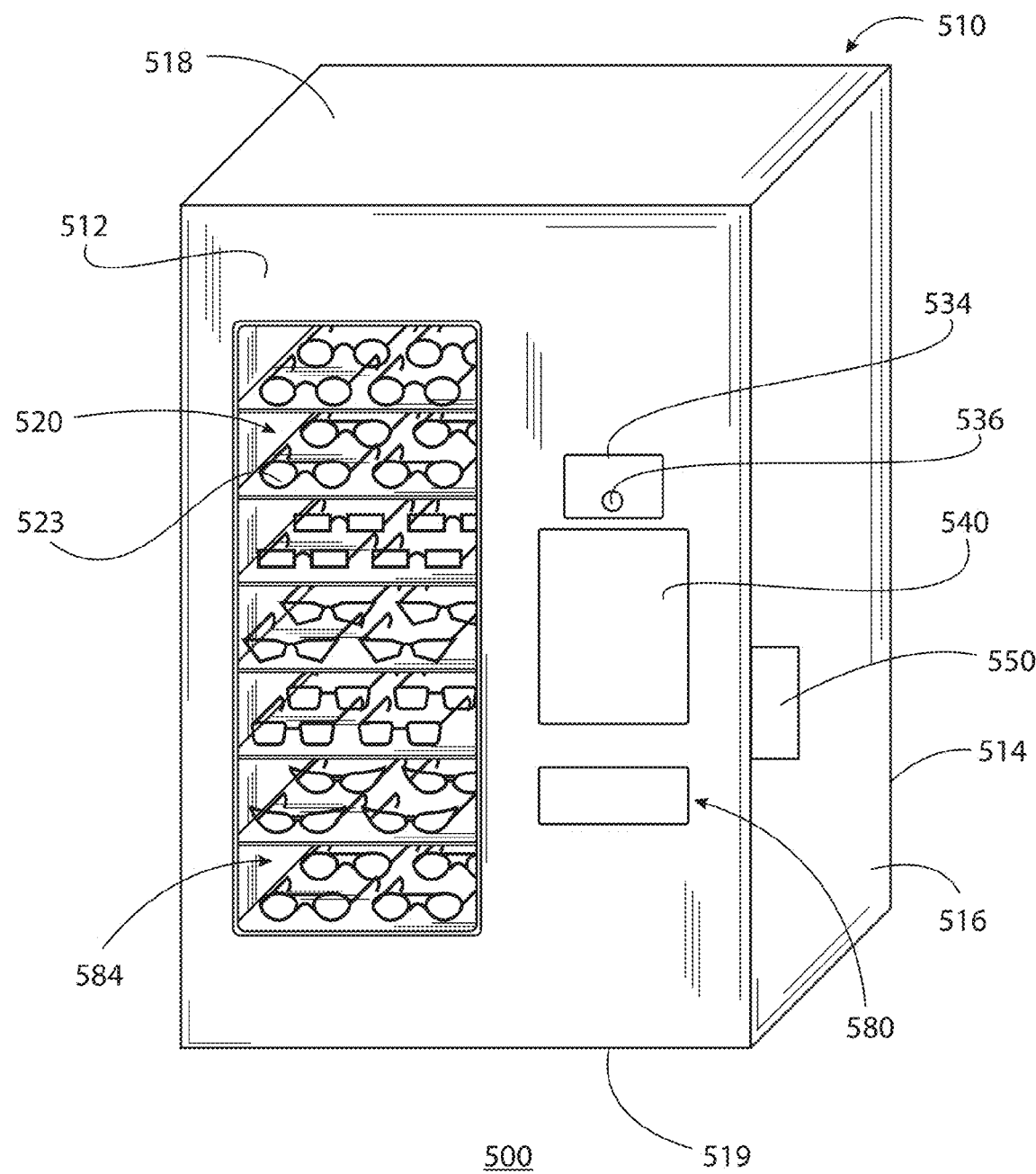
FIG. 5 is a perspective view of another exemplary embodiment of a corrective eyewear kiosk in accordance with the present invention.

Referring now primarily to FIG. 5, an alternative embodiment of a self-contained corrective eyewear electronic kiosk 500 is presented in a perspective view. The self-contained corrective eyewear electronic kiosk 500 includes a kiosk housing 510 substantially enclosing a frame support structure 520 supporting a plurality of eyeglass frames 523 and a camera 534. The kiosk housing 510 includes a front wall 512, a rear wall 514, a pair of opposing side walls 516, a roof 518, and a floor 519, collectively providing a substantial enclosure of the self-contained corrective eyewear electronic kiosk 500. The camera 534 includes a camera lens 536 provided at a front surface of the front wall 512 for capturing images of consumers wearing eyeglass frames 523 in accordance with the present invention.

The self-contained corrective eyewear electronic kiosk 500 can further include a display 540, a financial transaction unit 550, a frame dispenser 580, and a transparent window 584. The display 540, similar to the display 144, is provided at the front surface of the front wall 512 for displaying instructions to the consumer and allowing the consumer to input commands and information, as explained above with respect to the display 144. The financial transaction unit 550, similar to the financial transaction unit 150, can be provided at one of the side walls 516 or the front wall 512. The frame dispenser 580 includes an opening defined by the front wall 512 for dispensing a selected one of the plurality of eyeglass frames 523 to the consumer to try on. The frame dispenser 580 also allows for receiving and returning the selected eyeglass frame 523 into the enclosure provided by the kiosk housing 510, after the consumer has captured an image while wearing the selected eyeglass frame 523, or the consumer otherwise desires to return the eyeglass frame 523 to the electronic kiosk 500. The transparent window 584 can be integrated into the front wall 512 for allowing the consumer to view the plurality of eyeglass frames 523.

Advantageously, the self-contained corrective eyewear electronic kiosk 500 does not require employment of an attendant to man the electronic kiosk 500. Additionally, a security feature can be affixed to each of the plurality of eyeglass frames 523 to prevent theft. In further embodiments, the electronic kiosk 500 may be operably configured to require that the consumer provide a payment input or an identification input prior to the electronic kiosk 500 releasing the selected eyeglass frame 523 from the substantially enclosing kiosk housing 510. For example, the consumer may be prompted via the display 144 to swipe the consumer's credit card, debit card, driver's license, or other identification information, before receiving the selected eyeglass frame 523 from the frame dispenser 580. In this embodiment, the eyeglass frame 523 is not dispensed to the consumer unless and until such information is provided. This feature may deter theft and provide a method of tracking theft.

The eyeglass frame support 520 can be provided in the form of a rack, shelf, rotatable carousel, and the like. In some embodiments, the electronic kiosk 500 can include a robotic retrieval system that locates and retrieves the selected eyeglass frames 523 from predetermined positions on the frame support structure 520. The robotic retrieval system can include one or more robotic arms that are configured to retrieve the consumer-selected eyeglass frame 523 from the frame support structure 520 within the kiosk housing 510 and provide the frame 523 to the consumer via the frame dispenser 580. In one embodiment, each of the plurality of eyeglass frames 523 can be associated with an alphanumeric code that is displayed to the consumer and the consumer can input the alphanumeric code associated with a desired eyeglass frame 523 via the display 144, or other user input interface. After the alphanumeric code is entered into the user input interface, the robotic arm of the retrieval system can automatically move to retrieve the selected eyeglass frame 523. The robotic arm can include fingers configured to grip eyeglass frames 523. The robotic arm figures can release their grip such that the eyeglass frame 523 are delivered to the consumer via the frame dispenser 580.

In other embodiments, each of the plurality of eyeglass frames 523 can be associated with an alphanumeric code that is associated with each row, column, or rack to which the frames 523 are placed. In said manner, when a user selects the desired frame 523, the system associated with the electronic kiosk 500 is informed of the particular frame 523 selected by the user, including the corresponding dimensions of said frame 523. The association between the selected frame 523 and the dimensions can be triggered by alphanumeric code input by the user. In other embodiments, a switching mechanism that is coupled to each row/column/rack can be utilized. The switching mechanism can be activated upon selection, e.g., removal, of the frame 523 selected by the user. As will apparent to those of skill in the art, the switching mechanism may utilize electro-mechanical devices to relay a signal indicative of activation of the switching mechanism to the system associated with the electronic kiosk 500 for processing.

Figure 6:
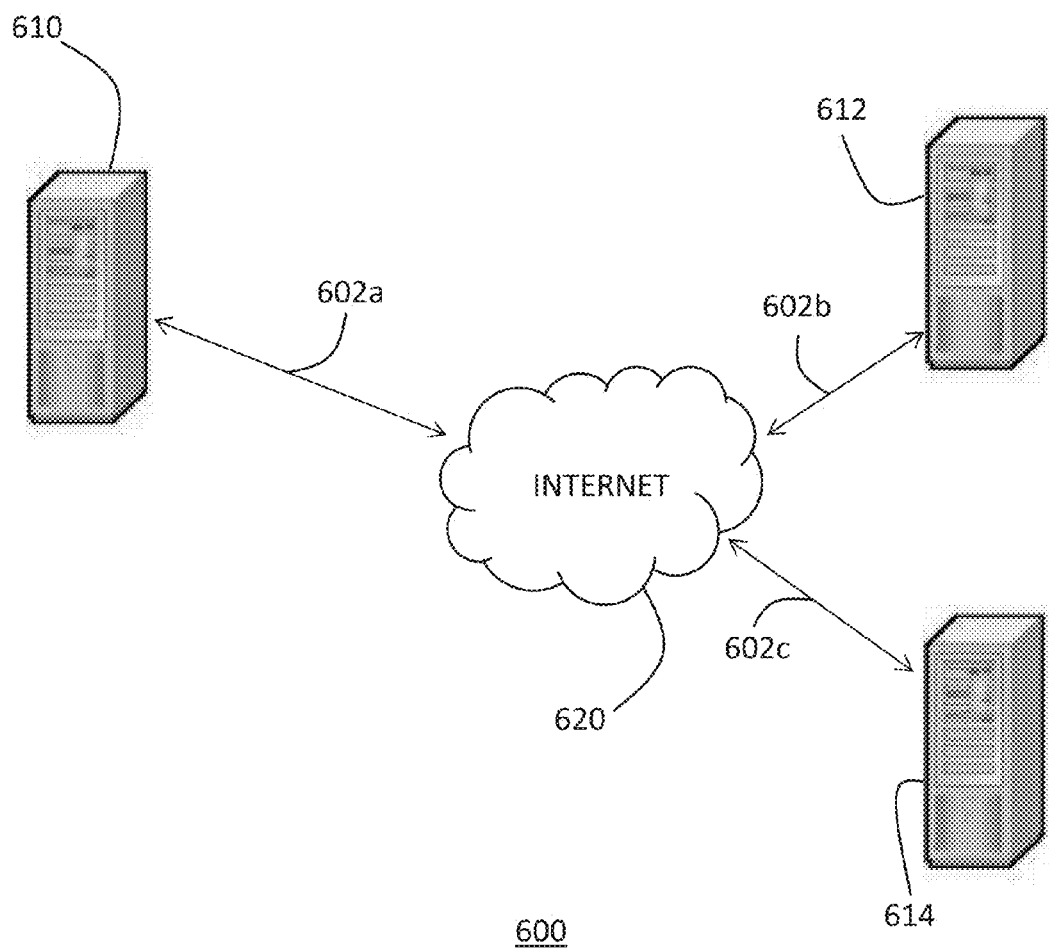
FIG. 6 is a block diagram of an exemplary distributed data processing network in accordance with an embodiment of the present invention.

Referring now primarily to FIG. 6, a representation of a network 600 in which the present invention may be implemented is illustrated. The network 600 includes connections 602*a-n*, which are the medium used to provide communication links between various devices, processing units, computers, or the like, which can be connected together within the network 600. The connections 602*a-n* may be wired or wireless connections. A few exemplary wired connections are cables, phone lines, and fiber optics. Exemplary wireless connections include radio frequency (RF) and infrared radiation (IR) transmissions. Many other wired and wireless connections are known in the art and can be used with the present invention.

In the depicted example, the network 600 includes an image capturing device 610, an image processing computer 612, and a laboratory computer 614. The image capturing device 610 can be a camera configured to capture images of consumers wearing eyeglass frames at the corrective eyewear electronic kiosk 100, 500. The image capturing device 610 can include non-volatile memory where the images are stored.

The image processing computer 612 can include a database where predetermined value(s) of reference dimension(s) 430 associated with each of the plurality of eyeglass frames 123 are stored. The image processing computer 612 further includes an executable instruction set stored in non-volatile or non-transitory memory of the image processing computer 612. The instruction set can be a software application that is adapted to receive an image captured at the electronic kiosk 100, 500 via the connections 602*a-b*, retrieve from the database predetermined value(s) of reference dimension(s) associated with the eyeglass frame 123 captured in the image, and determine the pupillary distance of the consumer captured in the image. The instruction set may also be adapted to identify the eyeglass frame 123 style using the image and obtaining a predetermined identification code associated with the identified frame 123 style from the database. In an alternative embodiment, the consumer may input an identification code associated with the consumer-selected eyeglass frame 123 style into a user input interface, such as the display 144 touchscreen. The identification code can subsequently be communicated to the image processing computer 612 in order to determine which eyeglass frame 123 style is desired by the consumer. In another embodiment, the image capturing device 610 can be included in the image processing computer 612 and both 610, 612 can be included in the electronic kiosk 100, 500. The identification code can be a serial number, a product code, a product name, or the like, associated with each eyeglass frame 123.

The laboratory computer 614 can be a computer associated with a laboratory, a manufacturer, and/or a distributor that makes or distributes corrective lenses and/or eyeglass frames. Prescription information input by the consumer 616 at the electronic kiosk 100, 500, pupillary distance measurements determined by the image processing computer 612, and an identification of the consumer-selected eyeglass frame 123 can be communicated to the laboratory computer 614 via the network connections 602a and 602c. The laboratory, manufacturer, and/or distributor can make or distribute the corrective lens and the consumer-selected eyeglass frame and mail the finished product to the consumer, or the kiosk vendor for pick-up.

In the depicted example, the network 600 can include the Internet 620, which represents a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, including thousands of commercial, government, educational and other computer systems that route data and messages. Of course, the network 600 may be implemented as a number of different types of networks, such as for example, an Intranet, a LAN, or a WAN. FIG. 6 is intended as an example, and not as an architectural limitation for the present invention.

Figure 7:
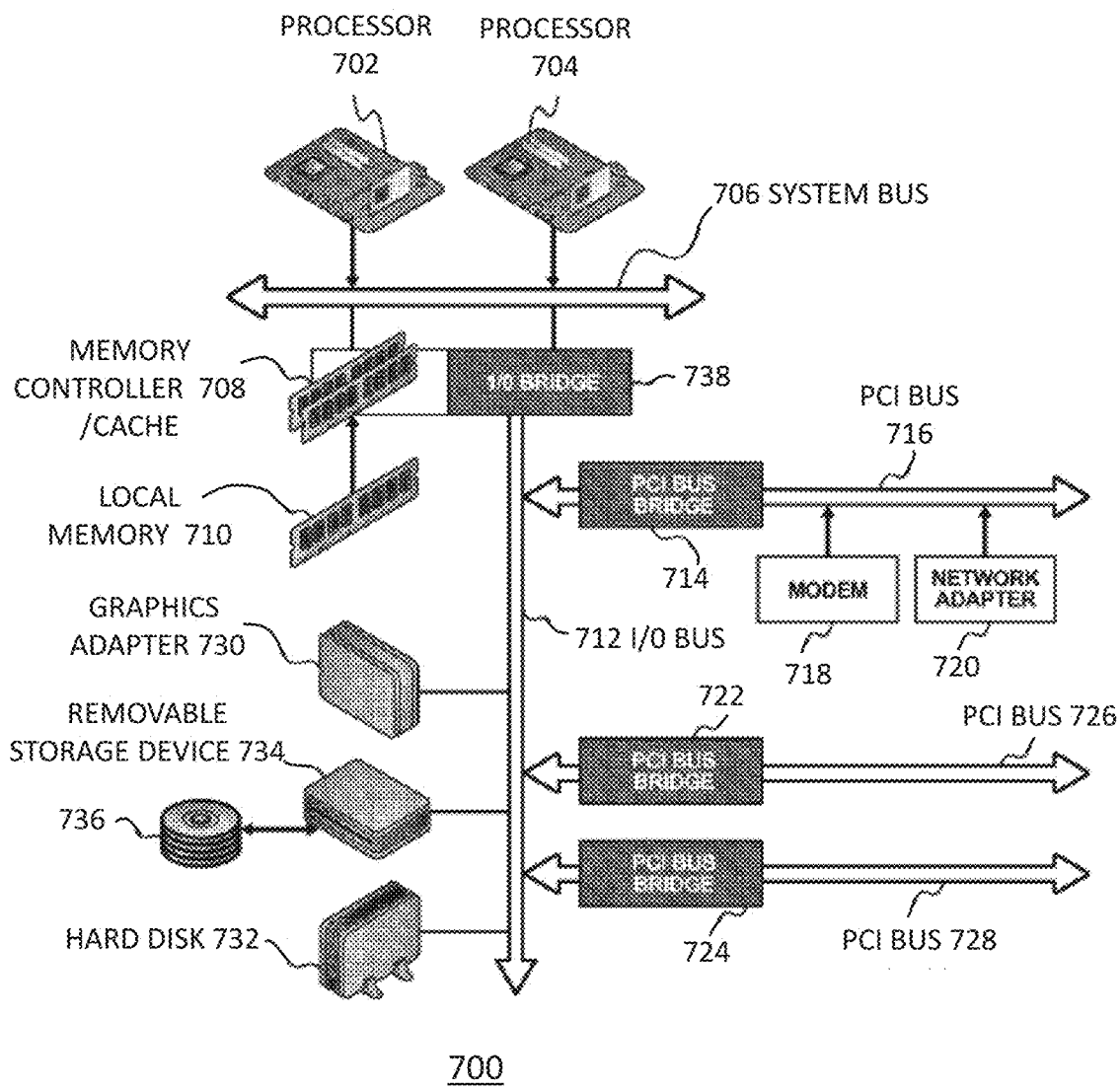
FIG. 7 is a block diagram of a data processing system that may be implemented as a network device, such as the image processing computer shown in FIG. 6, in accordance with an embodiment of the present invention.

Referring now primarily to FIG. 7, a block diagram of a data processing system 700 that may be implemented as a computer, such as the image processing computer 612, the transaction control unit 140, and the laboratory computer 614. The data processing system 700 may be a symmetric multiprocessor (SMP) system including a plurality of processors 702 and 704 connected to a system bus 706. Alternatively, a single processor system may be employed. Also, connected to the system bus 706 is a memory controller/cache 708, which provides an interface to local memory 710. An I/O bus bridge 738 is connected to the system bus 706 and provides an interface to an I/O bus 712. The memory controller/cache 708 and I/O bus bridge 738 may be integrated as depicted. The processor 702 or 704 in conjunction with the memory controller 708 controls what data is stored in memory 710. The processor 702 and/or 704 and memory controller 708 can serve as a data counter for counting the rate of data flow to the memory 710 or from the memory 710 and can also count the total volume of data accessed to or from the memory 710. The processor 702 or 704 can also work in conjunction with any other memory device or storage location.

Peripheral component interconnect (PCI) bus bridge 714 connected to the I/O bus 712 provides an interface to a PCI local bus 716. A number of modems 718, or wireless cards, may be connected to the PCI bus 716. Typical PCI bus implementations will support four PCI expansion slots or add-in connectors. PCI includes, but is not necessarily limited to, PCI-X and PCI Express components. Communication links to the network of computers in FIG. 6 may be provided through the modem 718 and a network adapter 720 connected to the PCI local bus 716 through add-in boards.

Additional PCI bus bridges 722 and 724 provide interfaces for additional PCI buses 726 and 728, from which additional modems or network adapters may be supported. In this manner, the data processing system 700 allows connections to multiple networks of computers. A graphics adapter 730 and a hard disk 732 may also be connected to the I/O bus 712 as depicted, either directly or indirectly.

Those of ordinary skill in the art will appreciate that the hardware depicted in FIG. 7 may vary. For example, other peripheral devices, such as optical disk drives or the like, also may be used in addition to or in place of the hardware depicted. The depicted example is not meant to imply architectural limitations with respect to the present invention.

In this document, the terms "computer program medium," "computer usable medium," and "computer readable medium" are used to generally refer to media such as main memory 710, a removable storage drive 734, removable media 736, hard disk 732, and signals. These computer program products are means for providing software to the computer system. The computer readable medium allows the computer system to read data, instructions, messages or message packets, and other computer readable information from the computer readable medium. The computer readable medium, for example, may include non-volatile memory, such as Floppy, ROM, Flash memory, Disk drive memory, CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired or wireless network that allows a computer to read such computer readable information.

Figure 8:
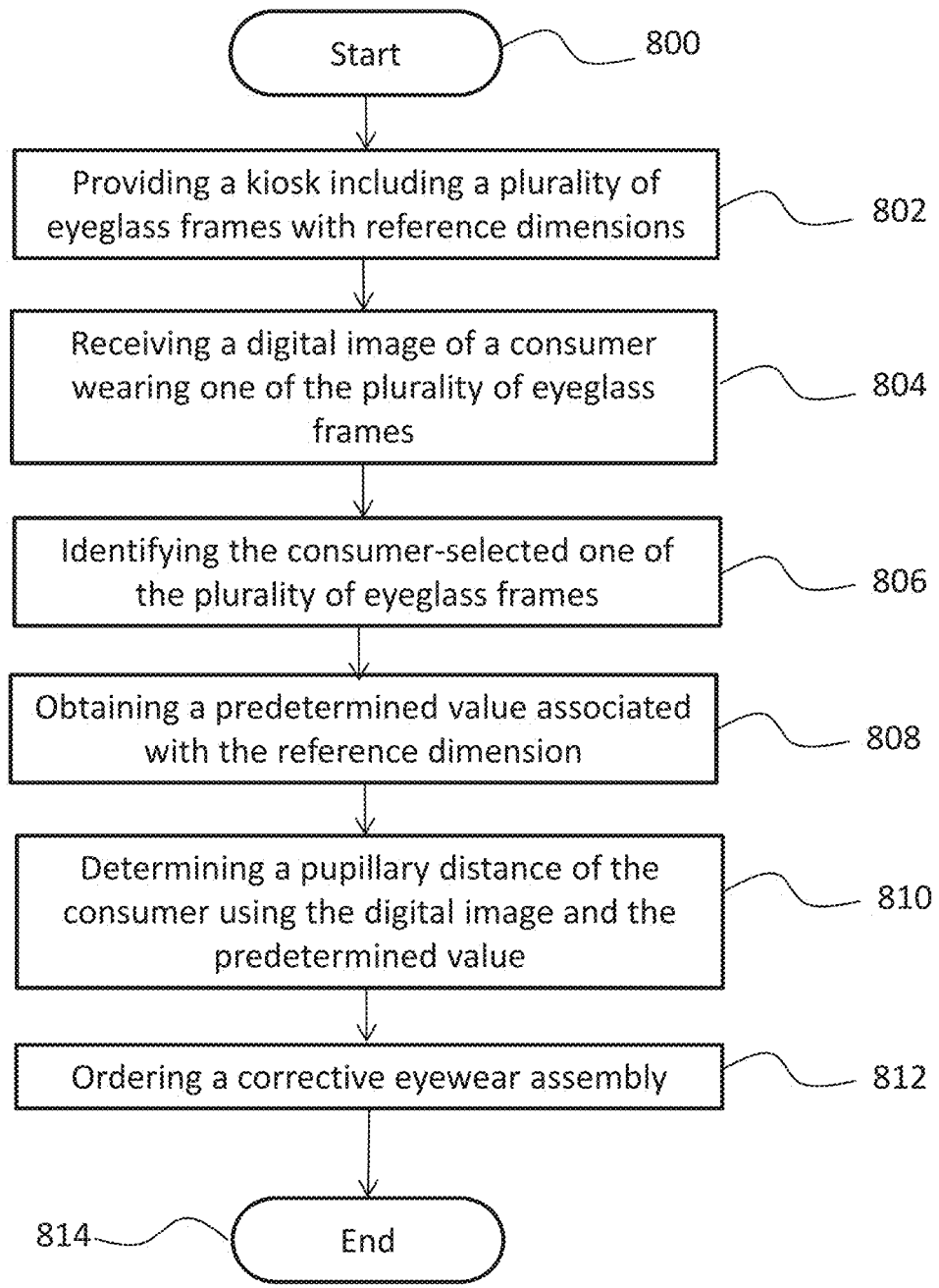
FIG. 8 is a process flow chart representing an exemplary method of providing corrective eyewear in accordance with the present invention.

Referring now primarily to FIG. 8, an exemplary logic flow for a method of providing corrective eyewear to the consumer 400 is illustrated. The process begins at step 800 and moves directly to step 802, where the electronic kiosk 100 is provided with a plurality of eyeglass frames 123. The electronic kiosk 100 is preferably provided in an area of high public traffic, such as a mall or a superstore. Advantageously, the electronic kiosk 100 can be provided at a retail location that does not employ an optician or other eye care professional, as with other prior-art methods of providing corrective eyewear to consumers 400. Each of the plurality of eyeglass frames 123 are different from one another in at least one of a dimension and a size. Each of the plurality of eyeglass frames 123 has at least one reference dimension 430 on a body of the eyeglass frame 123. In alternative embodiments, two or more reference dimensions 430 are provided on the body of the eyeglass frame 123. For example, the length of the front frame and the height of the front frame may both be used in a calculation to determine the pupillary distance 428 of the consumer 400. Using two or more reference dimensions may increase the accuracy of the value obtained from calculating the pupillary distance 428. Predetermined values representing each of the at least one reference dimensions 430 are stored at a database communicatively coupled to the electronic kiosk 100 and each predetermined value stored at the database is associated with a corresponding one of the plurality of eyeglass frames 123. The database can be provided in the transaction control unit 140 of the electronic kiosk 100 or the database can be provided at a remote location, such as a computer server connected to the network 600.

In step 804, a digital image of the consumer 400 wearing a consumer-selected one of the plurality of eyeglass frames 123 is received. The digital image can be stored in memory at the electronic kiosk 100. The at least one reference dimension 430 on the body of the consumer-selected eyeglass frame 123 and the pupils 410, 412 of the consumer 400 are visible in the digital image. In step 806, the consumer-selected eyeglass frame 123 is identified. The identification of the consumer-selected eyeglass frame 123 can be obtained by prompting the consumer 400 to input an identification code into a user input interface included in the electronic kiosk 100. The identification code can be provided by, for example, a tab or a label on the body of the corresponding eyeglass frames 123. In an alternative embodiment, the identification of the consumer-selected eyeglass frame 123 can be obtained by a computer processing the digital image, where the computer analyzes the digital image based on known, predetermined features of each of the plurality of eyeglass frames 123 in order to identify the particular eyeglass frame 123 depicted in the digital image. Advantageously, this eliminates the step of the consumer 400 manually inputting the identification code into the electronic kiosk 100.

In step 808, the predetermined value associated with the reference dimension of the identified consumer-selected eyeglass frame 123 is obtained from the database. The database can be a computer with memory, where the predetermined values of each of the reference dimensions are stored. The database can be located at the electronic kiosk 100 or at a remote location communicatively coupled to the electronic kiosk 100 over the network 600 via the connections 602.

In step 810, the pupillary distance 428 of the consumer 400 is mathematically calculated using the digital image and the predetermined value of the at least one reference dimension 430 of the consumer-selected eyeglass frame 123. The predetermined value of the at least one reference dimension 430 is a real-world value of the reference dimension 430, such as, for example, a 10 centimeter value for the length of the front frame, the length of the front frame being the reference dimension 430 and 10 centimeters being the real-world value. In one embodiment, this real-world value is used to scale the digital image. The scale value can be applied to the image to determine the real-world pupillary distance 428 between the pair of pupils 412, 410 captured in the digital image. For example, if the computer determines that the distance between pupils 412 and 410 captured in the digital image is one half the distance of the length of the front frame in the digital image, and the predetermined value of the front frame is 10 centimeters, then the real-world value of the pupillary distance 428 of the consumer 400 is 5 centimeters. Calculating the pupillary distance 428 of the consumer 400 based on the reference dimension 430 captured in the digital image is calculated where the object associated with the reference dimension 430 is the same distance from the camera lens as the consumer's face 400. Accordingly, providing the reference dimension 430 on the body of the eyeglass frame 123 in accordance with the present invention automatically satisfies this condition, because the consumer 400 is wearing the eyeglass frame 123 on his face in the digital image. Accordingly, the consumer 400 is not required to perform an extra step of positioning a separate object such that the object aligns with the consumer's face relative to the camera lens, which can introduce an element of human error into the mathematical calculation of the pupillary distance 428.

In step 812, an order is placed for a corrective eyeglass frame and lens assembly corresponding to the consumer-selected eyeglass frame 123 and the determined pupillary distance 428 of the consumer 400. An identifier associated with the consumer-selected eyeglass frame 123 and the calculated pupillary distance 428 of the consumer 400 is communicated to a computer, such as the computer 614, connected to the network 600 via, for example, connections 602. Subsequently, the identified eyeglass frame 123 can be manufactured or ordered according to the identifier of the consumer-selected eyeglass frame 123 and the lens can be prepared by a laboratory or a manufacturer according to the calculated pupillary distance 428 and prescription information provided by the consumer 400. In one embodiment, a manufacturer of the consumer-selected eyeglass frame 123 can receive, via the computer 614, the identifier associated with the consumer-selected eyeglass frame 123, which identifier may be in the form of a part number, alphanumeric code, the digital image of the consumer 400 captured at the electronic kiosk 100, or other identifier than can be used to identify the consumer-selected eyeglass frame 123 style. The manufacturer can then manufacture the consumer-selected eyeglass frame 123 and mail the eyeglass frame 123 to the consumer's address, the electronic kiosk 100 vendor, or a laboratory preparing the lens. The laboratory can receive data associated with preparing the lens, such as prescription information and the pupillary distance 428, via a computer, such as the computer 614. The laboratory can then prepare the lens using the pupillary distance 428 and prescription information to accurately correct the consumer's vision. After the lens is prepared, the laboratory can mail the lens to the consumer's address or the electronic kiosk 100 vendor. Prescription information can be input by the consumer 400 via the user input interface, such as the touchscreen display 144 included in the electronic kiosk 100. The process ends at step 814.

Figure 9:
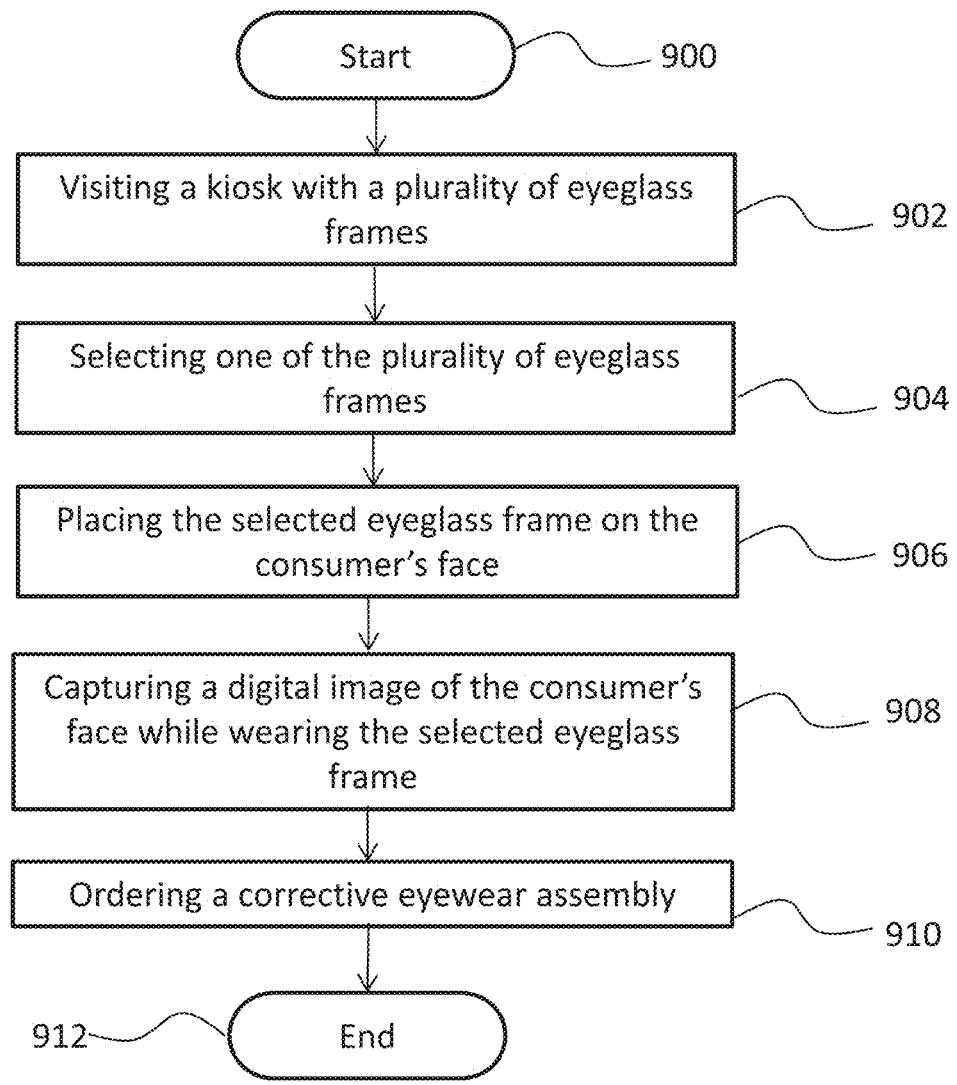
FIG. 9 is a process flow chart representing an exemplary method of ordering corrective eyewear in accordance with the present invention.

Referring now primarily to FIG. 9, an exemplary logic flow for a method of the consumer 400 ordering corrective eyewear via the electronic kiosk 100 is presented. The method begins at step 900 and moves directly to step 902, where the consumer 400 visits the electronic kiosk 100 at a retail location. The consumer 400 may travel to the electronic kiosk 100 at a retail location that does not employ an optician or other eye care professional associated with the electronic kiosk 100. In step 904, the consumer 400 selects one of the plurality of eyeglass frames 123 provided at the electronic kiosk 100, 500. In one embodiment, the consumer 400 can grasp the selected eyeglass frame 123 from the eyeglass frame support 120 by manually removing the eyeglass frame 123 from an open eyeglass frame carousel. In an alternative embodiment, the consumer can input an identification code of the selected eyeglass frame 523 via the touchscreen display 540 and receive the selected eyeglass frame 523 via the dispenser 580 of the self-contained electronic kiosk 500. In step 906, the consumer 400 places a chosen eyeglass frame 123 on the consumer's face 400. The consumer 400 may try on a multitude of eyeglass frame 123 styles from the eyeglass frame support 120 until he finally decides which frame 123 to select. The consumer may view himself with each of the eyeglass frames 123 via the viewing panel 132. By physically trying on the eyeglass frames 123, as opposed to merely selecting one online, the consumer 400 is able to feel the weight of the frame 123, the quality of the material that the frame 123 is constructed of, and obtain a real-world view of what the frame 123 looks like on the consumer's face in real-world lighting. At the same time, the electronic kiosk 100 provides a method of measuring the pupillary distance 428 without requiring the assistance of an optician or other eye care professional.

In step 908, once the consumer 400 has selected an eyeglass frame 123 style, the consumer 400 captures a digital still image of the consumer's face while wearing the selected eyeglass frame 123 via the image capturing unit 134 of the electronic kiosk 100. There may be a button, for example, on the touchscreen display 144 that the consumer 400 can press in order to capture the image. The consumer 400 may be given the option via the display 144 to capture more than one image and then select one image to process an order with.

In step 910, the consumer 400 orders the corrective eyewear assembly. The consumer 400 may be prompted via the display 144 to input prescription information, name, address, email address, or the like. The consumer 400 may be prompted to input an identification code associated with the selected eyeglass frame 123 via the user input interface at the electronic kiosk 100. The consumer 400 may be prompted to provide payment, by, for example, swiping a credit card or debit card via an electronic payment reader provided at the electronic kiosk 100. The consumer 400 may be queried, via the display 144, whether the consumer wants to receive correspondence via the email address. The consumer may be notified on the display 144 that coupons, specials, and/or other deals can be emailed to his email address. The consumer 400 may be notified via the display 144 that a confirmation email can be sent to his email address to verify that the corrective eyewear assembly has been mailed to the consumer-provided mailing address.

In one embodiment, the consumer 400 may be prompted to create a user account at the electronic kiosk 100. The consumer 400 can be prompted via the display 144 to create a username and a password. The electronic kiosk 100 can be configured to store all or some of the consumer information input into the electronic kiosk 100 via the user input interface and associate the consumer information with the user account. This allows the consumer 400 to return to the electronic kiosk 100 and order another corrective eyewear assembly using the pre-stored information associated with the user account that the consumer 400 created. In another embodiment, the network 600 can include a plurality of kiosks 100 connected to one another via connections 602, each electronic kiosk 100 located in a plurality of publicly accessible areas. User account information may be stored at a central server within the network 600. The central server allows user account information to be shared among the plurality of kiosks 100, such that the consumer 400 can log-in to his account at a first one of the plurality of kiosks 100 to order corrective eyewear assembly and, subsequently, the consumer 400 can log-in to his account at a second one of the plurality of kiosks 100 provided at a different location to order yet another corrective eyewear assembly.

When the order is near completion, the consumer 400 may be prompted via the display 144 to press a submit button in order to complete the order. The order can then be transmitted via connections 602 over the network 600 to a remotely located computer associated with a manufacturer, distributor, and/or laboratory that is able to make or order the selected eyeglass frame 123 and the corrective lens. The consumer may be prompted to input whether he prefers the corrective eyewear assembly to be mailed to his address or to the address associated with the electronic kiosk 100. The process ends at step 912.

Figure 10:
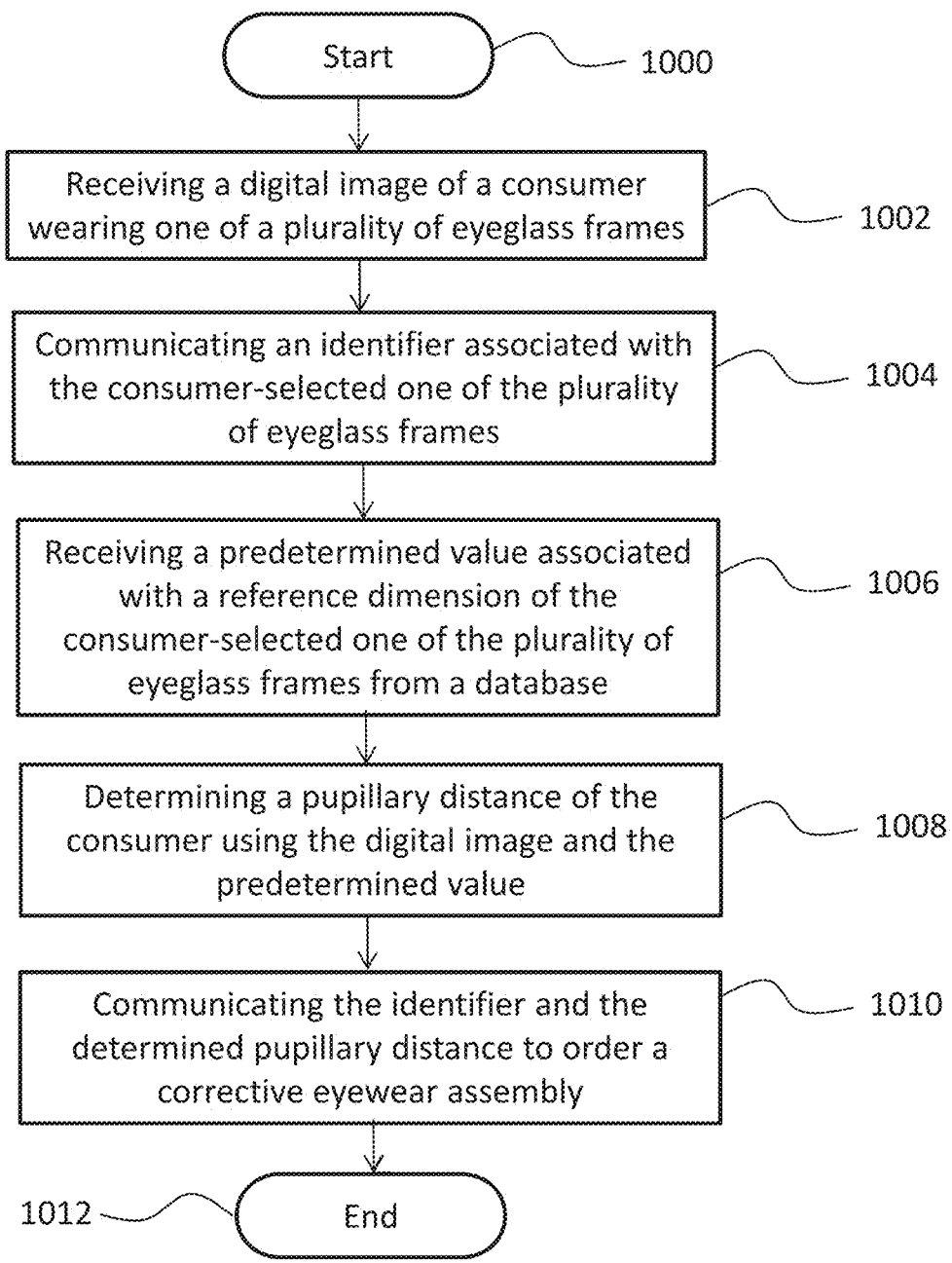
FIG. 10 is a process flow chart representing an exemplary method of determining pupillary distance, without a kiosk, in accordance with the present invention.

Referring now primarily to FIG. 10, an exemplary logic flow for a method of determining a consumer's pupillary distance, without a kiosk, to order corrective eyewear is presented. The process begins at step 1000 and immediately proceeds to step 1002, where an electronic device receives a digital image of a consumer wearing a consumer-selected one of a plurality of eyeglass frames. The electronic device is preferably a mobile electronic device, such as a cellular mobile device or a computer tablet. In another embodiment, the electronic device is a personal computer operating a web browser. The web browser can include a plugin including instructions for executing process steps described herein, in accordance with embodiments of the present invention. The digital image includes at least one reference dimension of the consumer-selected one of the plurality of eyeglass frames and a pair of pupils of the consumer. In step 1004, the electronic device communicates an identifier associated with the consumer-selected one of the plurality of eyeglass frames to a computer communicatively coupled to a database. The identifier may be in the form of a part number, an alphanumeric code, the digital image of the consumer captured by the electronic device, or any other identifier than can be used to identify the consumer-selected eyeglass frame style. The database stores at least one predetermined value of at least one reference dimension of each of the plurality of eyeglass frames. In one embodiment, the plurality of eyeglass frames varies in at least one of a dimension and a size from one another. The computer can be a server communicatively coupled to the electronic device via a wide area network, such as the Internet. In an alternative embodiment, the computer can be the electronic device itself, where the database is non-volatile memory of the electronic device communicatively coupled to a processor of the electronic device.

In step 1006, the electronic device receives a predetermined value of the reference dimension of the consumer-selected one of the plurality of eyeglass frames from the database. In one embodiment, the database is located remotely from the electronic device. The database can be located at a computer server communicatively coupled to the electronic device via a wide area network, such as the Internet. In an alternative embodiment, the database is stored in memory of the electronic device. The memory is preferably non-volatile memory. In step 1008, a pupillary distance of the consumer is determined based on the digital image and the predetermined value of the at least one reference dimension of the consumer-selected one of the plurality of eyeglass frames. In one embodiment, the electronic device determines the pupillary distance by calculating the pupillary distance using the digital image and the predetermined value of the reference dimension. In an alternative embodiment, the electronic device determines the pupillary distance by receiving the pupillary distance from a remotely located computer, such as the server, which calculates the pupillary distance.

In step 1010, the electronic device communicates the identifier and the determined pupillary distance to order a corrective eyewear assembly. In one embodiment, the electronic device communicates the identifier and the determined pupillary distance to a computer associated with a retail store that sells eyeglass frames for corrective eyewear. This allows the consumer to advantageously select eyeglass frames at a retail location, capture an image of himself wearing the selected eyeglass frame via a digital camera of his mobile electronic device, and immediately submit an order for corrective eyewear via the mobile electronic device to a computer associated with the retail location and communicatively coupled to the mobile electronic device via the Internet. This can eliminate the need for retail locations to allocate labor hours to eye care professionals to physically measure the consumer's pupillary distance. Moreover, it can eliminate the need for retail locations to use high-cost pupillary distance measuring machines. And, consumers can more quickly and easily order corrective eyewear, discretely, with a few clicks of a button. The process ends at step 1012.

FIGS. 8-10 show a specific order of executing functional logic steps, the order of executing the steps may be changed relative to the order shown and described. Also, two or more steps shown in succession may be executed concurrently or with partial concurrence. Certain steps may also be omitted for the sake of brevity. And some steps are merely exemplary steps in an exemplary implementation, but are not required in order to be in accordance with the present invention. The steps can be implemented as a computer program product including a computer readable storage medium having a computer readable instruction set embodied therein. The computer readable instruction set can include instructions executed by a processor for implementing the steps.

A system, assembly, and method has been disclosed that allows consumers to conveniently order corrective eyewear without the assistance of an optician or other eye care professional and to obtain accurate pupillary distance measurements while, at the same time, maintaining the benefit of being able to physically try on various eyeglass frames styles at convenient retail locations that the consumer likely visits on a regular basis.

The invention claimed is:

1. An electronic kiosk assembly for ordering corrective eyewear, the electronic kiosk assembly including:
    an eyeglass frame support supporting a plurality of physical eyeglass frames, the plurality of physical eyeglass frames varying in at least one of a dimension and a size from one another and each of the plurality of physical eyeglass frames having at least one reference dimension defined by a body of the physical eyeglass frame;
    an image capturing element;
    a processor communicatively coupled to the image capturing element;
    a memory coupled to the processor and having a database storing a predetermined value of the at least one reference dimension defined by the body of the physical eyeglass frame for each of the plurality of physical eyeglass frames;
    a set of computer instructions stored in the memory and executable by the processor, the set of computer instructions including instructions for:
    receiving, at the processor, a digital image, captured by the image capturing element, of a consumer wearing a consumer-selected one of the plurality of physical eyeglass frames;
    interpreting, by the processor, the digital image to determine the at least one reference dimension defined by the consumer-selected one of the plurality of physical eyeglass frames and to locate a pair of pupils of the consumer in the digital image;
    determining, by the processor, a distance between the pair of pupils of the consumer in the digital image;
    determining, by the processor, an image scale ratio by comparing the at least one reference dimension determined by the processor by interpreting the digital image to the predetermined value of the at least one reference dimension stored in the database; the predetermined value of the at least one reference dimension stored in the database before the digital image is captured by the image capturing element;
    determining the real-world pupillary distance of the consumer by applying the image scale ratio to the distance between the pair of pupils of the consumer in the digital image; and
    transmitting by an output coupled to the processor eyeglass manufacturing information including an identifier associated with the consumer-selected one of the plurality of eyeglass frames and the real-world pupillary distance of the consumer, the real-world pupillary distance is a pupillary distance value that is output to an eyeglass manufacturer via the output coupled to the processor in order to manufacture a corrective eyewear.

2. The electronic kiosk assembly in accordance with claim 1, wherein the electronic kiosk assembly further includes an image capturing device behind a two-way mirror.

3. The electronic kiosk assembly in accordance with claim 1, wherein the electronic kiosk assembly is a self-contained unit substantially enclosed by a housing.

4. The electronic kiosk assembly in accordance with claim 3, wherein the set of computer instructions further includes instructions for requiring the consumer to provide at least one of a payment input and an identification input prior to the electronic kiosk releasing the consumer-selected one of the plurality of physical eyeglass frames from the housing.

5. The electronic kiosk assembly in accordance with claim 1, wherein the electronic kiosk assembly further includes a viewing panel, an image capturing unit, a transaction control unit, and a financial transaction unit.

* * * * *